United States Patent
Hack et al.

(10) Patent No.: US 11,552,278 B2
(45) Date of Patent: Jan. 10, 2023

(54) INTEGRATED PHOTOBIOMODULATION DEVICE

(71) Applicant: Universal Display Corporation, Ewing, NJ (US)

(72) Inventors: Michael Hack, Carmel, CA (US); Michael Stuart Weaver, Princeton, NJ (US); Julia J. Brown, Yardley, PA (US)

(73) Assignee: Universal Display Corporation, Ewing, NJ (US)

(*) Notice: Subject to any disclaimer, the term of this patent is extended or adjusted under 35 U.S.C. 154(b) by 213 days.

(21) Appl. No.: 16/404,775

(22) Filed: May 7, 2019

(65) Prior Publication Data
US 2019/0348628 A1 Nov. 14, 2019

Related U.S. Application Data

(60) Provisional application No. 62/668,285, filed on May 8, 2018.

(51) Int. Cl.
*H01L 51/52* (2006.01)
*H01L 25/04* (2014.01)
(Continued)

(52) U.S. Cl.
CPC ........ *H01L 51/5278* (2013.01); *H01L 25/048* (2013.01); *H01L 27/3209* (2013.01);
(Continued)

(58) Field of Classification Search
CPC .............. H01L 25/0756; H01L 25/048; H01L 27/3209; H01L 51/504; H01L 51/5044;
(Continued)

(56) References Cited

U.S. PATENT DOCUMENTS

| 4,769,292 A | 9/1988 | Tang |
|---|---|---|
| 5,247,190 A | 9/1993 | Friend |

(Continued)

FOREIGN PATENT DOCUMENTS

| CN | 109670367 A | * | 4/2019 |
|---|---|---|---|
| WO | 2008057394 A1 | | 5/2008 |
| WO | 2010011390 A2 | | 1/2010 |

OTHER PUBLICATIONS

English Translation of KR 10-2018-0008359. (Year: 2018).*

(Continued)

*Primary Examiner* — Yu Chen
(74) *Attorney, Agent, or Firm* — Butzel Long

(57) ABSTRACT

Embodiments of the disclosed subject matter may provide a display device or display surface including at least one emissive layer and a near-infrared (NIR) emissive layer disposed in a stack arrangement between a first electrode and a second electrode, where NIR light is emitted from the NIR emissive layer through the at least one emissive layer, or visible light is emitted from the at least one emissive layer through the NIR emissive layer, and where the NIR light output by the NIR emissive layer has a peak wavelength of 740 nm-1000 nm. Embodiments of the disclosed subject matter may provide a near infrared (NIR) light source disposed behind or in front of an active-matrix organic light emitting diode (AMOLED), where the NIR light source has an area greater than 25% of an active area of the display device or display surface.

6 Claims, 6 Drawing Sheets

(51) Int. Cl.
*H01L 27/32* (2006.01)
*A61N 5/06* (2006.01)

(52) U.S. Cl.
CPC ............... *A61N 2005/0634* (2013.01); *A61N 2005/0653* (2013.01); *A61N 2005/0659* (2013.01)

(58) Field of Classification Search
CPC ........ H01L 51/5278; A61N 2005/0659; A61N 2005/0653
See application file for complete search history.

(56) References Cited

U.S. PATENT DOCUMENTS

| | | | |
|---|---|---|---|
| 5,703,436 | A | 12/1997 | Forrest |
| 5,707,745 | A | 1/1998 | Forrest |
| 5,834,893 | A | 11/1998 | Bulovic |
| 5,844,363 | A | 12/1998 | Gu |
| 6,013,982 | A | 1/2000 | Thompson |
| 6,087,196 | A | 7/2000 | Sturm |
| 6,091,195 | A | 7/2000 | Forrest |
| 6,097,147 | A | 8/2000 | Baldo |
| 6,294,398 | B1 | 9/2001 | Kim |
| 6,303,238 | B1 | 10/2001 | Thompson |
| 6,337,102 | B1 | 1/2002 | Forrest |
| 6,468,819 | B1 | 10/2002 | Kim |
| 7,279,704 | B2 | 10/2007 | Walters |
| 7,431,968 | B1 | 10/2008 | Shtein |
| 7,968,146 | B2 | 6/2011 | Wagner |
| 8,766,531 | B1 | 7/2014 | Hack |
| 9,385,172 | B2 | 7/2016 | Hack |
| 2003/0230980 | A1 | 12/2003 | Forrest |
| 2004/0174116 | A1 | 9/2004 | Lu |
| 2014/0065290 | A1* | 3/2014 | Lewis ................ B82Y 30/00 427/1 |
| 2016/0359117 | A1* | 12/2016 | Hamade ............. H01L 51/0052 |
| 2017/0229663 | A1 | 8/2017 | Tsai |
| 2019/0096959 | A1* | 3/2019 | Lee ..................... H01L 27/3213 |
| 2019/0140031 | A1* | 5/2019 | Lamkin ............. H01L 27/14669 |
| 2019/0290929 | A1* | 9/2019 | Jiao ....................... H01L 51/504 |
| 2021/0036047 | A1* | 2/2021 | Heo .................... H01L 51/5278 |

OTHER PUBLICATIONS

Hashmi et al., "Effect of Pulsing in Low-Level Light Therapy", Aug. 2010, Lasers Surg Med, 42(6), 450-466 (Year: 2010).*

Henderson et al., "Near-infrared photonic energy penetration: can infrared phototherapy effectively reach the human brians?", Aug. 21, 2015, Neuropsychiatric Disease and Treatment 2015:II, 2191-2208 (Year: 2015).*

Hipskind et al., "Pulsed Transcranial Red/Near-Infrared Light Therapy Using Light-Emitting Diodes Improves Cerebral Blood Flow and Cognitive Function in Veterans with Chronic Traumatic Brain Injury: A Case Series", Nov. 28, 2018, Photomedicine and Laser Surgery, 1-8 (Year: 2018).*

Wunsch et al., "A Controlled Trial to Determine the Efficacy of Red and Near-Infrared Light Treatment in Patient Satisfaction, Reduction of Fine Lines, Wrinkles, Skin Roughness, and Intradermal Collagen Density Increase", 2014, Photomedicine and Laser Surgery, vol. 32, No. 3, 93-100 (Year: 2014).*

Baldo et al. Highly efficient phosphorescent emission from organic electroluminescent devices, Nature, vol. 395, pp. 151-154, 1998.

Baldo, et al., "Very high-efficiency green organic light-emitting devices based on electrophosphorescence", Applied Physics Letters, Jul. 5, 1999, 4 pp., vol. 75, No. 1, American Institute of Physics, Melville, NY, USA.

* cited by examiner

INTEGRATED PHOTOBIOMODULATION DEVICE

CROSS-REFERENCE TO RELATED APPLICATIONS

This application claims priority to U.S. Patent Application Ser. No. 62/668,285, filed May 8, 2018, the entire contents of which are incorporated herein by reference.

FIELD

The present invention relates to integrating OLED based photobiomodulation light sources into common everyday objects (such as laptops, whiteboards, eye glasses, monitors, or the like) to provide the necessary light exposure to improve health through photobiomodulation.

BACKGROUND

Opto-electronic devices that make use of organic materials are becoming increasingly desirable for a number of reasons. Many of the materials used to make such devices are relatively inexpensive, so organic opto-electronic devices have the potential for cost advantages over inorganic devices. In addition, the inherent properties of organic materials, such as their flexibility, may make them well suited for particular applications such as fabrication on a flexible substrate. Examples of organic opto-electronic devices include organic light emitting diodes/devices (OLEDs), organic phototransistors, organic photovoltaic cells, and organic photodetectors. For OLEDs, the organic materials may have performance advantages over conventional materials. For example, the wavelength at which an organic emissive layer emits light may generally be readily tuned with appropriate dopants.

OLEDs make use of thin organic films that emit light when voltage is applied across the device. OLEDs are becoming an increasingly interesting technology for use in applications such as flat panel displays, illumination, and backlighting. Several OLED materials and configurations are described in U.S. Pat. Nos. 5,844,363, 6,303,238, and 5,707,745, which are incorporated herein by reference in their entirety.

One application for phosphorescent emissive molecules is a full color display. Industry standards for such a display call for pixels adapted to emit particular colors, referred to as "saturated" colors. In particular, these standards call for saturated red, green, and blue pixels. Alternatively the OLED can be designed to emit white light. In conventional liquid crystal displays emission from a white backlight is filtered using absorption filters to produce red, green and blue emission. The same technique can also be used with OLEDs. The white OLED can be either a single EML device or a stack structure. Color may be measured using CIE coordinates, which are well known to the art.

As used herein, the term "organic" includes polymeric materials as well as small molecule organic materials that may be used to fabricate organic opto-electronic devices. "Small molecule" refers to any organic material that is not a polymer, and "small molecules" may actually be quite large. Small molecules may include repeat units in some circumstances. For example, using a long chain alkyl group as a substituent does not remove a molecule from the "small molecule" class. Small molecules may also be incorporated into polymers, for example as a pendent group on a polymer backbone or as a part of the backbone. Small molecules may also serve as the core moiety of a dendrimer, which consists of a series of chemical shells built on the core moiety. The core moiety of a dendrimer may be a fluorescent or phosphorescent small molecule emitter. A dendrimer may be a "small molecule," and it is believed that all dendrimers currently used in the field of OLEDs are small molecules.

As used herein, "top" means furthest away from the substrate, while "bottom" means closest to the substrate. Where a first layer is described as "disposed over" a second layer, the first layer is disposed further away from substrate. There may be other layers between the first and second layer, unless it is specified that the first layer is "in contact with" the second layer. For example, a cathode may be described as "disposed over" an anode, even though there are various organic layers in between.

As used herein, "solution processible" means capable of being dissolved, dispersed, or transported in and/or deposited from a liquid medium, either in solution or suspension form.

A ligand may be referred to as "photoactive" when it is believed that the ligand directly contributes to the photoactive properties of an emissive material. A ligand may be referred to as "ancillary" when it is believed that the ligand does not contribute to the photoactive properties of an emissive material, although an ancillary ligand may alter the properties of a photoactive ligand.

As used herein, and as would be generally understood by one skilled in the art, a first "Highest Occupied Molecular Orbital" (HOMO) or "Lowest Unoccupied Molecular Orbital" (LUMO) energy level is "greater than" or "higher than" a second HOMO or LUMO energy level if the first energy level is closer to the vacuum energy level. Since ionization potentials (IP) are measured as a negative energy relative to a vacuum level, a higher HOMO energy level corresponds to an IP having a smaller absolute value (an IP that is less negative). Similarly, a higher LUMO energy level corresponds to an electron affinity (EA) having a smaller absolute value (an EA that is less negative). On a conventional energy level diagram, with the vacuum level at the top, the LUMO energy level of a material is higher than the HOMO energy level of the same material. A "higher" HOMO or LUMO energy level appears closer to the top of such a diagram than a "lower" HOMO or LUMO energy level.

As used herein, and as would be generally understood by one skilled in the art, a first work function is "greater than" or "higher than" a second work function if the first work function has a higher absolute value. Because work functions are generally measured as negative numbers relative to vacuum level, this means that a "higher" work function is more negative. On a conventional energy level diagram, with the vacuum level at the top, a "higher" work function is illustrated as further away from the vacuum level in the downward direction. Thus, the definitions of HOMO and LUMO energy levels follow a different convention than work functions.

More details on OLEDs, and the definitions described above, can be found in U.S. Pat. No. 7,279,704, which is incorporated herein by reference in its entirety.

SUMMARY

According to an embodiment, an organic light emitting diode/device (OLED) is provided. The OLED can include an anode, a cathode, and an organic layer, disposed between the anode and the cathode. According to an embodiment, the organic light emitting device is incorporated into one or more devices, such as a consumer product, an electronic component module, and/or a lighting panel.

According to an embodiment, a device may include a first electrode, a second electrode, and a display device or display surface including at least one emissive layer and a near-infrared (NIR) emissive layer disposed in a stack arrangement between the first electrode and the second electrode. The NIR light output by the NIR emissive layer may have a peak wavelength of 740 nm-1000 nm. More than 50% of energy output of the NIR emissive layer may have a wavelength greater than 750 nm.

The device may include at least one charge generation layer disposed between the at least one emissive layer and the NIR emissive layer, or disposed between each of the emissive layers when the at least one emissive layer includes two or more emissive layers. The device may include at least one additional electrode disposed between the first electrode and the second electrode, where the NIR emissive layer is separately controllable from the at least one emissive layer.

The device may include a third electrode and a fourth electrode, where the third electrode and the fourth electrode are disposed between the first electrode and the second electrode. An insulator may be disposed between the NIR layer of the stack arrangement and the at least one emissive layer.

The at least one emissive layer of the device may be a red (R) emissive layer, a green (G) emissive layer, a blue (B) emissive layer, a yellow emissive layer (Y), and/or a white emissive layer (W). At least one emissive layer may be at least semi-transparent.

The NIR light output by the NIR emissive layer of the device may be a continuous wave having a predetermined optical power, or may be pulsed NIR light that may have a pulse frequency that is different from a frame rate or a clock frequency of the display device or the display surface.

The NIR light may be output by the NIR emissive layer when the device is connected to an electrical power source other than a battery, where the electrical power source is connected to NIR pixels of the NIR emissive layer. A voltage of the electrical power source may determine an output energy of the NIR emissive layer. The NIR emissive layer may output the NIR light at a predetermined period of a day.

The maximum power density of the display device or the display surface for the NIR emissive layer may be 200 mW/cm$^2$. The optical power output of the NIR emissive layer per unit area of the display device or the display surface may be 2-200 mW/cm$^2$.

According to an embodiment, a device may include a display device or display surface including at least one emissive layer, where at least a portion of the at least one emissive layer includes a NIR emissive region. The at least one emissive layer may be disposed between a pair of electrodes, the NIR light output by the NIR emissive region may have a peak wavelength of 740 nm-1000 nm. The at least one emissive layer may include a plurality of subpixels that may be red sub-pixels, green sub-pixels, blue sub-pixels, yellow sub-pixels, and/or white sub-pixels.

More than 50% of energy output of the NIR emissive region of the device may have a wavelength greater than 750 nm. The NIR light output by the NIR emissive region may be a continuous wave having a predetermined optical power, or may be pulsed NIR light that has a pulse frequency that is different from a frame rate or a clock frequency of the display device or the display surface. The NIR light may be output by the NIR emissive region when the device is connected to an electrical power source other than a battery. The electrical power source may be connected to NIR pixels of the NIR emissive region, and a voltage of the electrical power source may determine an output energy of the NIR emissive region. The NIR emissive region of the device may output the NIR light at a predetermined period of a day.

The maximum power density of the display device or the display surface for the NIR emissive region may be 200 mW/cm$^2$. The optical power output of the NIR emissive region per unit area of the display device or the display surface may be 2-200 mW/cm$^2$.

According to an embodiment, a device may include a display device or display surface having an active-matrix organic light emitting diode (AMOLED), and a near infrared (NIR) light source disposed behind or in front of the AMOLED. The NIR light source may have an area greater than 25% of an active area of the display device or display surface. In some embodiments, a near infrared (NIR) light source may be disposed in front of the AMOLED, and a circular polarizer may be disposed between the AMOLED and the NIR light source.

The NIR light source may be transparent to visible light when the AMOLED is disposed behind the NW light source. The AMOLED may be transparent to NIR emission when the NIR light source is disposed behind the AMOLED.

The transparent AMOLED may include transparent organic light emitting devices (OLEDs), and/or top emission OLEDs with transparent regions disposed between emissive regions.

The transparent AMOLED may include switchable mirror anodes. When there is no NIR light output from the NIR light source, OLED anodes may be reflective to providing top emission microcavity OLED output. When the display device is off, and the NIR light source has output, the OLED anodes may be configured to be transparent to increase transparency.

The NIR light source may be patterned within each pixel of the display device or the display surface. The NIR light source may include an outcoupling device that may be disposed between the NIR light source and the display device.

The display device may be configured to be transparent by using transparent sub-pixels, and/or transparent regions between the sub-pixels. The red sub-pixels of the display device may include a transparent anode, and green and blue sub-pixels of the display device include a microcavity.

The device may include a heat dissipation device configured to dissipate heat from the NIR light source.

The NIR light source may output continuous wave or pulsed NIR light that has a pulse frequency that is different from a frame rate or a clock frequency of the display device or the display surface. The NIR light source may be segmented into regions, and each region may be illuminated in sequence. The NIR light source may output NIR light when the device is connected to electrical power source other than a battery. The electrical power source may be connected to NIR pixels of the NIR light source, and a voltage of the electrical power source may determine an output energy of the NIR light source. The NIR light source may output NIR light at a predetermined period of a day. The NIR light source may be an OLED (organic light emitting device) light source, a Quantum Dot light source, and/or a micro-LED (light emitting device) source. NIR light output by the NIR light source may have a peak wavelength of 740 nm-1000 nm. More than 50% of energy output of the NIR source may have a wavelength greater than 750 nm.

DETAILED DESCRIPTION

Generally, an OLED comprises at least one organic layer disposed between and electrically connected to an anode and a cathode. When a current is applied, the anode injects holes and the cathode injects electrons into the organic layer(s). The injected holes and electrons each migrate toward the oppositely charged electrode. When an electron and hole localize on the same molecule, an "exciton," which is a localized electron-hole pair having an excited energy state, is formed. Light is emitted when the exciton relaxes via a photoemissive mechanism. In some cases, the exciton may be localized on an excimer or an exciplex. Non-radiative mechanisms, such as thermal relaxation, may also occur, but are generally considered undesirable.

The initial OLEDs used emissive molecules that emitted light from their singlet states ("fluorescence") as disclosed, for example, in U.S. Pat. No. 4,769,292, which is incorporated by reference in its entirety. Fluorescent emission generally occurs in a time frame of less than 10 nanoseconds.

More recently, OLEDs having emissive materials that emit light from triplet states ("phosphorescence") have been demonstrated. Baldo et al., "Highly Efficient Phosphorescent Emission from Organic Electroluminescent Devices," Nature, vol. 395, 151-154, 1998; ("Baldo-I") and Baldo et al., "Very high-efficiency green organic light-emitting devices based on electrophosphorescence," Appl. Phys. Lett., vol. 75, No. 3, 4-6 (1999) ("Baldo-II"), are incorporated by reference in their entireties. Phosphorescence is described in more detail in U.S. Pat. No. 7,279,704 at cols. 5-6, which are incorporated by reference.

Figure 1:
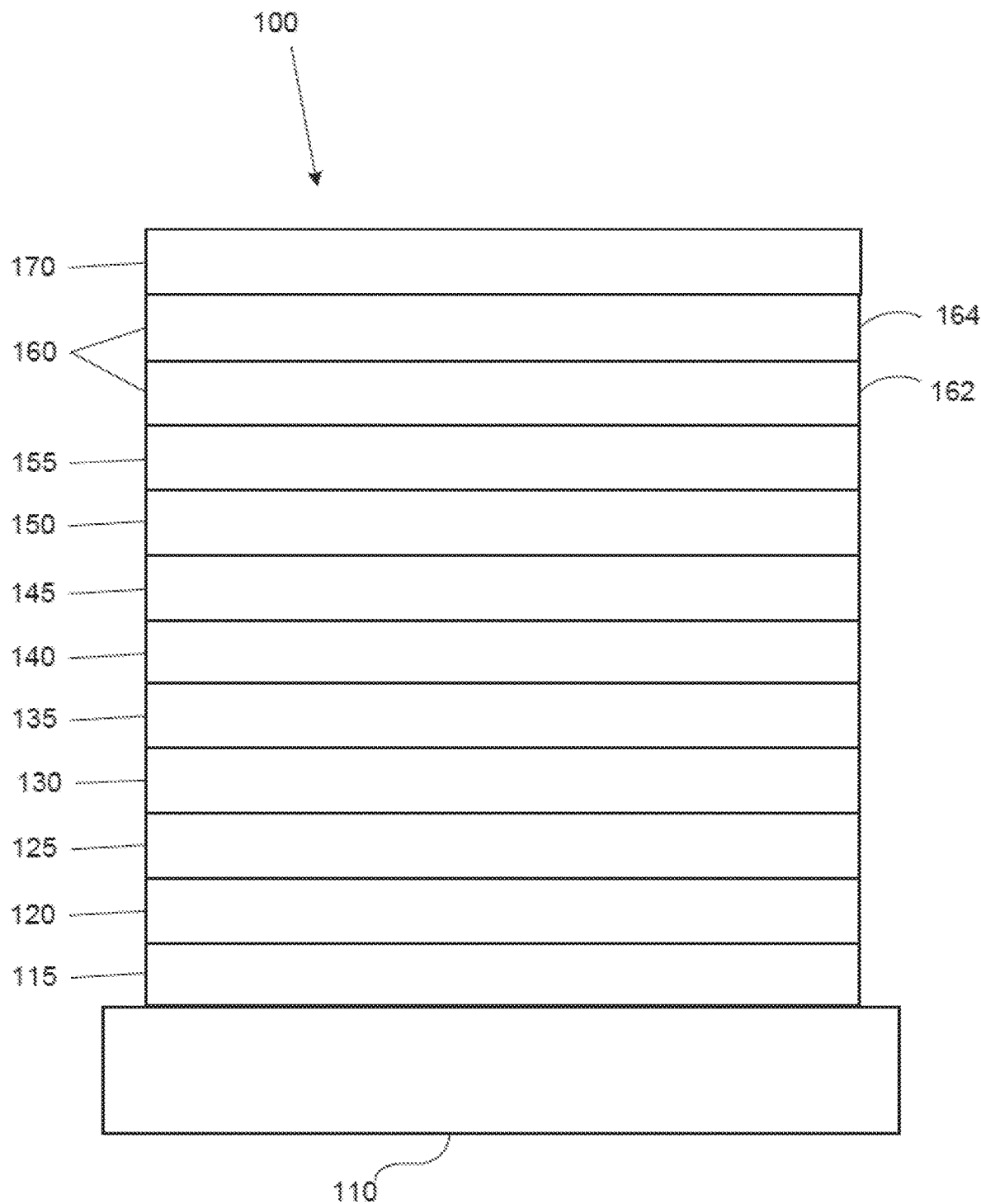
FIG. 1 shows an organic light emitting device.

FIG. 1 shows an organic light emitting device 100. The figures are not necessarily drawn to scale. Device 100 may include a substrate 110, an anode 115, a hole injection layer 120, a hole transport layer 125, an electron blocking layer 130, an emissive layer 135, a hole blocking layer 140, an electron transport layer 145, an electron injection layer 150, a protective layer 155, a cathode 160, and a barrier layer 170. Cathode 160 is a compound cathode having a first conductive layer 162 and a second conductive layer 164. Device 100 may be fabricated by depositing the layers described, in order. The properties and functions of these various layers, as well as example materials, are described in more detail in U.S. Pat. No. 7,279,704 at cols. 6-10, which are incorporated by reference.

More examples for each of these layers are available. For example, a flexible and transparent substrate-anode combination is disclosed in U.S. Pat. No. 5,844,363, which is incorporated by reference in its entirety. An example of a p-doped hole transport layer is m-MTDATA doped with $F_4$-TCNQ at a molar ratio of 50:1, as disclosed in U.S. Patent Application Publication No. 2003/0230980, which is incorporated by reference in its entirety. Examples of emissive and host materials are disclosed in U.S. Pat. No. 6,303,238 to Thompson et al., which is incorporated by reference in its entirety. An example of an n-doped electron transport layer is BPhen doped with Li at a molar ratio of 1:1, as disclosed in U.S. Patent Application Publication No. 2003/0230980, which is incorporated by reference in its entirety. U.S. Pat. Nos. 5,703,436 and 5,707,745, which are incorporated by reference in their entireties, disclose examples of cathodes including compound cathodes having a thin layer of metal such as Mg:Ag with an overlying transparent, electrically-conductive, sputter-deposited ITO layer. The theory and use of blocking layers is described in more detail in U.S. Pat. No. 6,097,147 and U.S. Patent Application Publication No. 2003/0230980, which are incorporated by reference in their entireties. Examples of injection layers are provided in U.S. Patent Application Publication No. 2004/0174116, which is incorporated by reference in its entirety. A description of protective layers may be found in U.S. Patent Application Publication No. 2004/0174116, which is incorporated by reference in its entirety.

Figure 2:
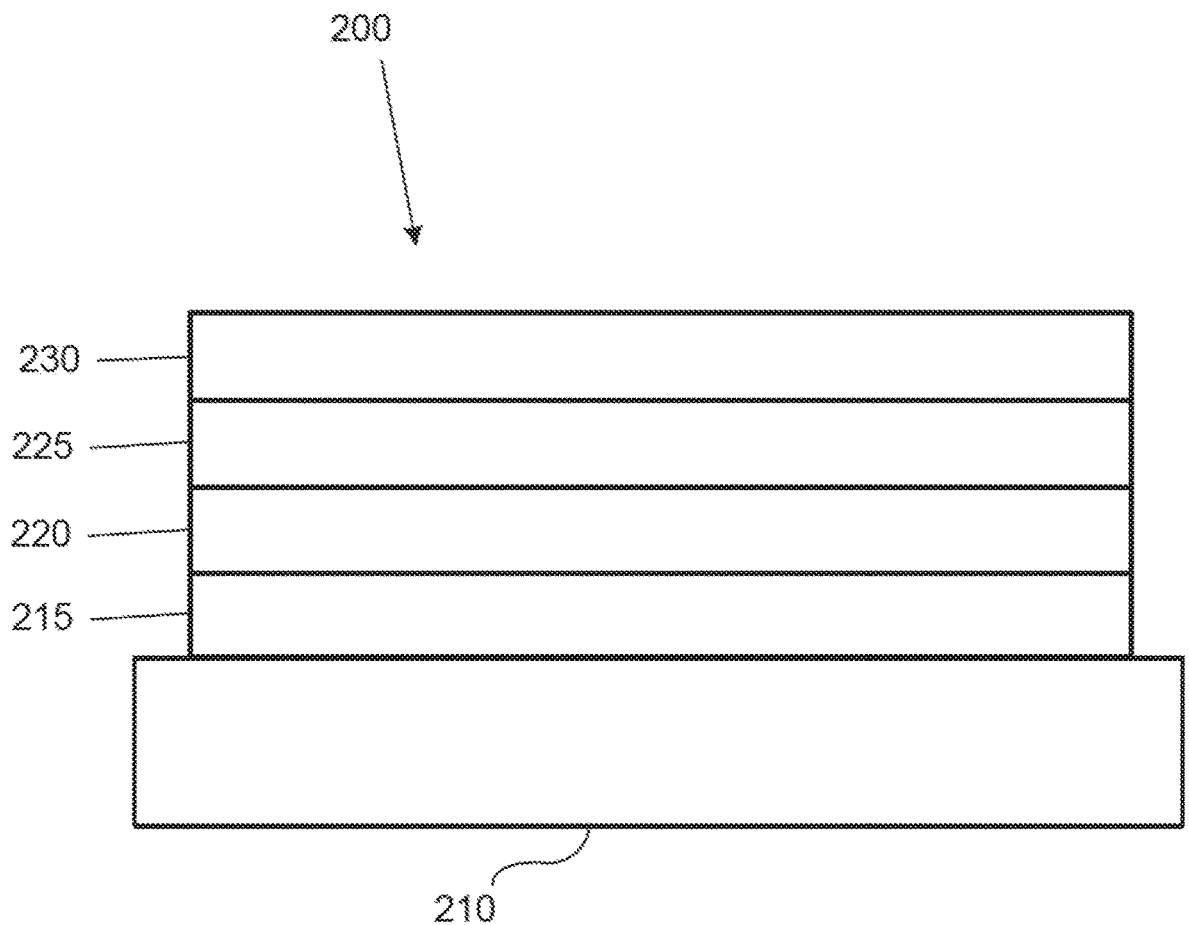
FIG. 2 shows an inverted organic light emitting device that does not have a separate electron transport layer.

FIG. 2 shows an inverted OLED 200. The device includes a substrate 210, a cathode 215, an emissive layer 220, a hole transport layer 225, and an anode 230. Device 200 may be fabricated by depositing the layers described, in order. Because the most common OLED configuration has a cathode disposed over the anode, and device 200 has cathode 215 disposed under anode 230, device 200 may be referred to as an "inverted" OLED. Materials similar to those described with respect to device 100 may be used in the corresponding layers of device 200. FIG. 2 provides one example of how some layers may be omitted from the structure of device 100.

The simple layered structure illustrated in FIGS. 1 and 2 is provided by way of non-limiting example, and it is understood that embodiments of the invention may be used in connection with a wide variety of other structures. The specific materials and structures described are exemplary in nature, and other materials and structures may be used. Functional OLEDs may be achieved by combining the various layers described in different ways, or layers may be omitted entirely, based on design, performance, and cost factors. Other layers not specifically described may also be included. Materials other than those specifically described may be used. Although many of the examples provided herein describe various layers as comprising a single material, it is understood that combinations of materials, such as a mixture of host and dopant, or more generally a mixture, may be used. Also, the layers may have various sublayers. The names given to the various layers herein are not intended to be strictly limiting. For example, in device 200, hole transport layer 225 transports holes and injects holes into emissive layer 220, and may be described as a hole transport layer or a hole injection layer. In one embodiment, an OLED may be described as having an "organic layer" disposed between a cathode and an anode. This organic layer may comprise a single layer, or may further comprise multiple layers of different organic materials as described, for example, with respect to FIGS. 1 and 2.

Structures and materials not specifically described may also be used, such as OLEDs comprised of polymeric materials (PLEDs) such as disclosed in U.S. Pat. No. 5,247,190 to Friend et al., which is incorporated by reference in its entirety. By way of further example, OLEDs having a single organic layer may be used. OLEDs may be stacked, for example as described in U.S. Pat. No. 5,707,745 to Forrest et al, which is incorporated by reference in its entirety. The OLED structure may deviate from the simple layered structure illustrated in FIGS. 1 and 2. For example, the substrate may include an angled reflective surface to improve outcoupling, such as a mesa structure as described in U.S. Pat. No. 6,091,195 to Forrest et al., and/or a pit structure as described in U.S. Pat. No. 5,834,893 to Bulovic et al., which are incorporated by reference in their entireties.

Unless otherwise specified, any of the layers of the various embodiments may be deposited by any suitable method. For the organic layers, preferred methods include thermal evaporation, ink-jet, such as described in U.S. Pat. Nos. 6,013,982 and 6,087,196, which are incorporated by reference in their entireties, organic vapor phase deposition (OVPD), such as described in U.S. Pat. No. 6,337,102 to Forrest et al., which is incorporated by reference in its entirety, and deposition by organic vapor jet printing (OVJP), such as described in U.S. Pat. No. 7,431,968, which is incorporated by reference in its entirety. Other suitable deposition methods include spin coating and other solution based processes. Solution based processes are preferably carried out in nitrogen or an inert atmosphere. For the other layers, preferred methods include thermal evaporation. Preferred patterning methods include deposition through a mask, cold welding such as described in U.S. Pat. Nos. 6,294,398 and 6,468,819, which are incorporated by reference in their entireties, and patterning associated with some of the deposition methods such as ink-jet and OVJD. Other methods may also be used. The materials to be deposited may be modified to make them compatible with a particular deposition method. For example, substituents such as alkyl and aryl groups, branched or unbranched, and preferably containing at least 3 carbons, may be used in small molecules to enhance their ability to undergo solution processing. Substituents having 20 carbons or more may be used, and 3-20 carbons is a preferred range. Materials with asymmetric structures may have better solution processability than those having symmetric structures, because asymmetric materials may have a lower tendency to recrystallize. Dendrimer substituents may be used to enhance the ability of small molecules to undergo solution processing.

Devices fabricated in accordance with embodiments of the present invention may further optionally comprise a barrier layer. One purpose of the barrier layer is to protect the electrodes and organic layers from damaging exposure to harmful species in the environment including moisture, vapor and/or gases, etc. The barrier layer may be deposited over, under or next to a substrate, an electrode, or over any other parts of a device including an edge. The barrier layer may comprise a single layer, or multiple layers. The barrier layer may be formed by various known chemical vapor deposition techniques and may include compositions having a single phase as well as compositions having multiple phases. Any suitable material or combination of materials may be used for the barrier layer. The barrier layer may incorporate an inorganic or an organic compound or both. The preferred barrier layer comprises a mixture of a polymeric material and a non-polymeric material as described in U.S. Pat. No. 7,968,146, PCT Pat. Application Nos. PCT/US2007/023098 and PCT/US2009/042829, which are herein incorporated by reference in their entireties. To be considered a "mixture", the aforesaid polymeric and non-polymeric materials comprising the barrier layer should be deposited under the same reaction conditions and/or at the same time. The weight ratio of polymeric to non-polymeric material may be in the range of 95:5 to 5:95. The polymeric material and the non-polymeric material may be created from the same precursor material. In one example, the mixture of a polymeric material and a non-polymeric material consists essentially of polymeric silicon and inorganic silicon.

Devices fabricated in accordance with embodiments of the invention can be incorporated into a wide variety of electronic component modules (or units) that can be incorporated into a variety of electronic products or intermediate components. Examples of such electronic products or intermediate components include display screens, lighting devices such as discrete light source devices or lighting panels, etc. that can be utilized by the end-user product manufacturers. Such electronic component modules can optionally include the driving electronics and/or power source(s). Devices fabricated in accordance with embodiments of the invention can be incorporated into a wide variety of consumer products that have one or more of the electronic component modules (or units) incorporated therein. A consumer product comprising an OLED that includes the compound of the present disclosure in the organic layer in the OLED is disclosed. Such consumer products would include any kind of products that include one or more light source(s) and/or one or more of some type of visual displays. Some examples of such consumer products include flat panel displays, computer monitors, medical monitors, televisions, billboards, lights for interior or exterior illumination and/or signaling, heads-up displays, fully or partially transparent displays, flexible displays, laser printers, telephones, mobile phones, tablets, phablets, personal digital assistants (PDAs), wearable devices, laptop computers, digital cameras, camcorders, viewfinders, microdisplays (displays that are less than 2 inches diagonal), 3-D displays, virtual reality or augmented reality displays, vehicles, video walls comprising multiple displays tiled together, theater or stadium screen, and a sign. Various control mechanisms may be used to control devices fabricated in accordance with the present invention, including passive matrix and active matrix. Many of the devices are intended for use in a temperature range comfortable to humans, such as 18 C to 30 C, and more preferably at room temperature (20-25 C), but could be used outside this temperature range, for example, from −40 C to 80 C.

The materials and structures described herein may have applications in devices other than OLEDs. For example, other optoelectronic devices such as organic solar cells and organic photodetectors may employ the materials and structures. More generally, organic devices, such as organic transistors, may employ the materials and structures.

In some embodiments, the OLED has one or more characteristics, such as being flexible, being rollable, being foldable, being stretchable, and/or being curved. In some embodiments, the OLED is transparent or semi-transparent. In some embodiments, the OLED further comprises a layer comprising carbon nanotubes.

In some embodiments, the OLED further comprises a layer comprising a delayed fluorescent emitter. In some embodiments, the OLED comprises a RGB pixel arrangement or white plus color filter pixel arrangement. In some embodiments, the OLED is a mobile device, a hand held device, or a wearable device. In some embodiments, the OLED is a display panel having less than 10 inch diagonal or 50 square inch area. In some embodiments, the OLED is a display panel having at least 10 inch diagonal or 50 square inch area. In some embodiments, the OLED is a lighting panel.

In some embodiments of the emissive region, the emissive region further comprises a host.

In some embodiments, the compound can be an emissive dopant. In some embodiments, the compound can produce emissions via phosphorescence, fluorescence, thermally activated delayed fluorescence, i.e., TADF (also referred to as E-type delayed fluorescence), triplet-triplet annihilation, or combinations of these processes.

The OLED disclosed herein can be incorporated into one or more of a consumer product, an electronic component module, and a lighting panel. The organic layer can be an emissive layer and the compound can be an emissive dopant in some embodiments, while the compound can be a non-emissive dopant in other embodiments.

The organic layer can also include a host. In some embodiments, two or more hosts are preferred. In some embodiments, the hosts used maybe a) bipolar, b) electron transporting, c) hole transporting or d) wide band gap materials that play little role in charge transport. In some embodiments, the host can include a metal complex. The host can be an inorganic compound.

Combination with Other Materials

The materials described herein as useful for a particular layer in an organic light emitting device may be used in combination with a wide variety of other materials present in the device. For example, emissive dopants disclosed herein may be used in conjunction with a wide variety of hosts, transport layers, blocking layers, injection layers, electrodes and other layers that may be present. The materials described or referred to below are non-limiting examples of materials that may be useful in combination with the compounds disclosed herein, and one of skill in the art can readily consult the literature to identify other materials that may be useful in combination.

Various materials may be used for the various emissive and non-emissive layers and arrangements disclosed herein. Examples of suitable materials are disclosed in U.S. Patent Application Publication No. 2017/0229663, which is incorporated by reference in its entirety.

Conductivity Dopants

A charge transport layer can be doped with conductivity dopants to substantially alter its density of charge carriers, which will in turn alter its conductivity. The conductivity is increased by generating charge carriers in the matrix material, and depending on the type of dopant, a change in the Fermi level of the semiconductor may also be achieved. Hole-transporting layer can be doped by p-type conductivity dopants and n-type conductivity dopants are used in the electron-transporting layer.

HIL/HTL

A hole injecting/transporting material to be used in the present invention is not particularly limited, and any compound may be used as long as the compound is typically used as a hole injecting/transporting material.

EBL

An electron blocking layer (EBL) may be used to reduce the number of electrons and/or excitons that leave the emissive layer. The presence of such a blocking layer in a device may result in substantially higher efficiencies, and or longer lifetime, as compared to a similar device lacking a blocking layer. Also, a blocking layer may be used to confine emission to a desired region of an OLED. In some embodiments, the EBL material has a higher LUMO (closer to the vacuum level) and/or higher triplet energy than the emitter closest to the EBL interface. In some embodiments, the EBL material has a higher LUMO (closer to the vacuum level) and or higher triplet energy than one or more of the hosts closest to the EBL interface. In one aspect, the compound used in EBL contains the same molecule or the same functional groups used as one of the hosts described below.

Host

The light emitting layer of the organic EL device of the present invention preferably contains at least a metal complex as light emitting material, and may contain a host material using the metal complex as a dopant material. Examples of the host material are not particularly limited, and any metal complexes or organic compounds may be used as long as the triplet energy of the host is larger than that of the dopant. Any host material may be used with any dopant so long as the triplet criteria is satisfied.

HBL

A hole blocking layer (HBL) may be used to reduce the number of holes and/or excitons that leave the emissive layer. The presence of such a blocking layer in a device may result in substantially higher efficiencies and/or longer lifetime as compared to a similar device lacking a blocking layer. Also, a blocking layer may be used to confine emission to a desired region of an OLED. In some embodiments, the HBL material has a lower HOMO (further from the vacuum level) and or higher triplet energy than the emitter closest to the HBL interface. In some embodiments, the HBL material has a lower HOMO (further from the vacuum level) and or higher triplet energy than one or more of the hosts closest to the HBL interface.

ETL

An electron transport layer (ETL) may include a material capable of transporting electrons. The electron transport layer may be intrinsic (undoped), or doped. Doping may be used to enhance conductivity. Examples of the ETL material are not particularly limited, and any metal complexes or organic compounds may be used as long as they are typically used to transport electrons.

Charge Generation Layer (CGL)

In tandem or stacked OLEDs, the CGL plays an essential role in the performance, which is composed of an n-doped layer and a p-doped layer for injection of electrons and holes, respectively. Electrons and holes are supplied from the CGL and electrodes. The consumed electrons and holes in the CGL are refilled by the electrons and holes injected from the cathode and anode, respectively; then, the bipolar currents reach a steady state gradually. Typical CGL materials include n and p conductivity dopants used in the transport layers.

OLED lighting may be used as a source of illumination for photobiomodulation therapy to benefit human health. Presently, devices are available which can provide red or near infra-red light. However, such devices are cumbersome, intrusive, and require a user to actively use them for periods of minutes or hours per day. Embodiments of the disclosed subject matter provide devices to expose users to the near infra-red radiation without them explicitly having to take any action. The embodiments of the disclosed subject matter may integrate an OLED photobiomodulation source into a device in front of which, users place part of their body. For example, OLED photobiomodulation light sources may be integrated into a laptop screen, mobile phone, television display, computer monitor, or the like so that users may receive photobiomodulation therapy during normal use of these devices. In some embodiments, devices that include photobiomodulation light sources having at least an 8 inch diagonal may provide a sufficient amount of light over a predetermined area of the human body.

Figure 3:
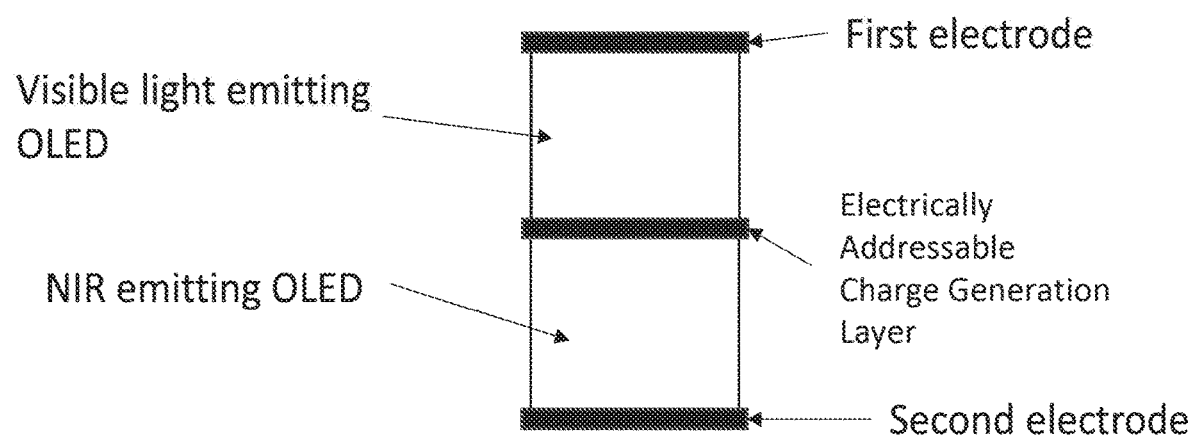
FIG. 3 shows a device stack surface including an emissive layer and a near-infrared (NIR) emissive layer disposed between a first electrode and a second electrode according to an embodiment of the disclosed subject matter.

In an embodiment of the disclosed subject matter, OLED pixels may be integrated into a display active area. For example, FIG. 3 shows a visibly emitting OLED in a stack arrangement with a NIR emitting OLED. The OLED pixels may emit at a desired wavelength or range of wavelengths for photobiomodulation, such as 740 nm-1000 nm. In some embodiments, the OLED pixels may emit a peak wavelength of 760-1000 nm, 780-1000 nm, 800-900 nm, 800-1000 nm, or the like.

Figure 5:
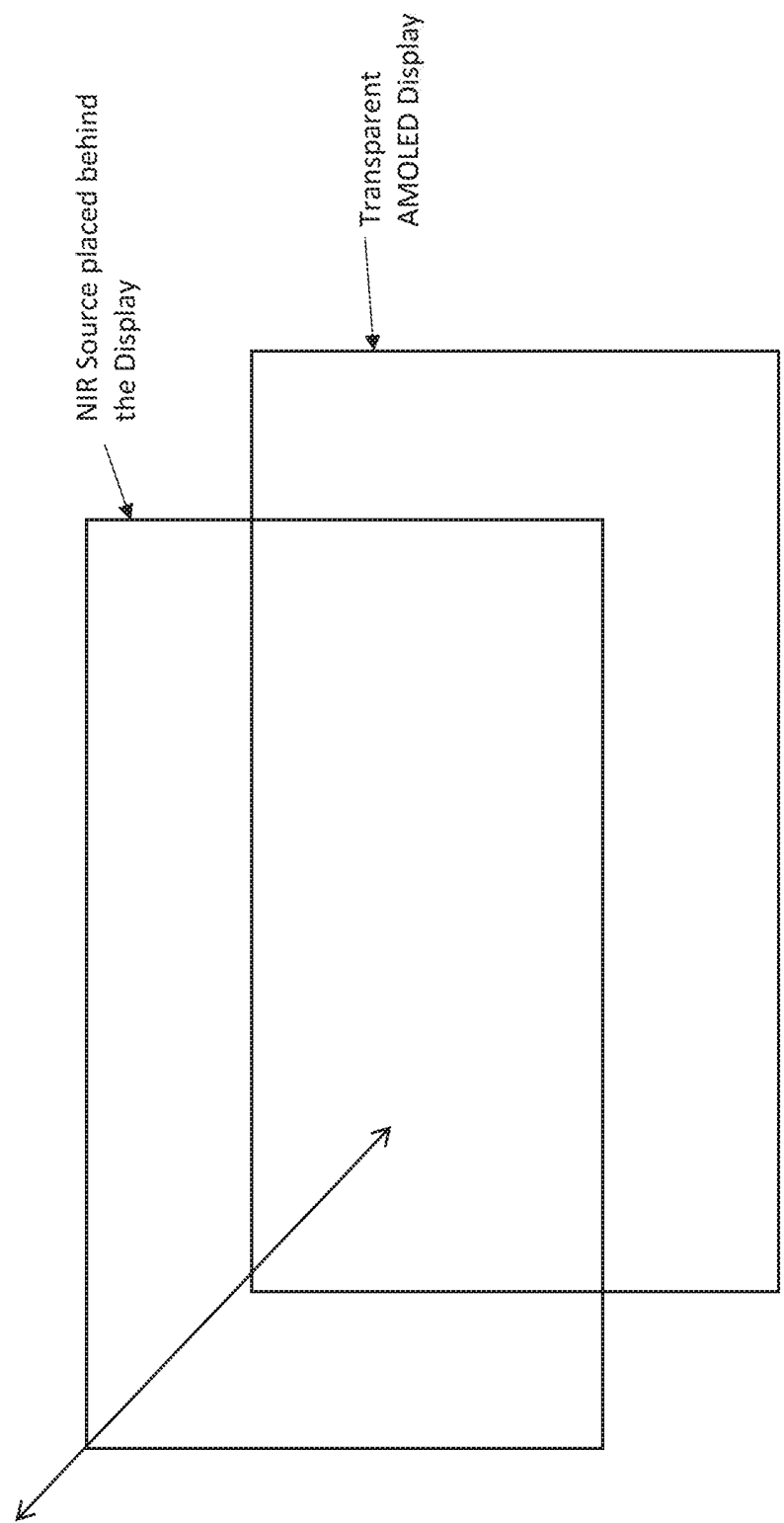
FIG. 5 shows a display device having a transparent active-matrix organic light emitting diode (AMOLED), and a near infrared (NIR) light source disposed behind the AMOLED according to an embodiment of the disclosed subject matter.
Figure 6:
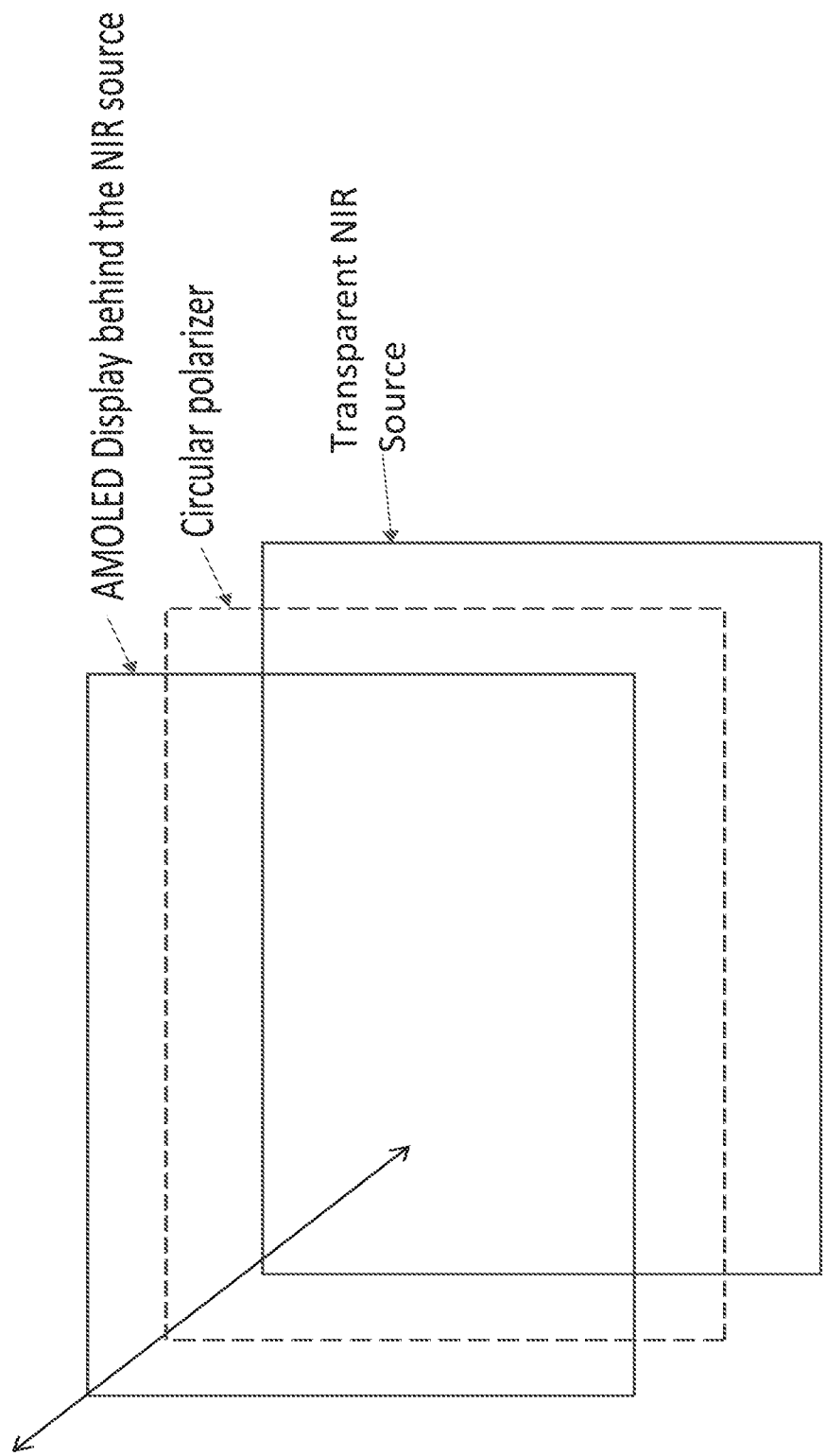
FIG. 6 shows a display device having an active-matrix organic light emitting diode (AMOLED), a near infrared (NIR) light source disposed in front of the AMOLED, and a circular polarizer disposed between the AMOLED and the NIR light source according to an embodiment of the disclosed subject matter.

In another embodiment of the disclosed subject matter, an OLED lamp (e.g., near infra-red (NIR) light source) may emit a desired wavelength or range of wavelengths for photobiomodulation, where the lamp may be a portion of a display. For example, FIG. 5 shows a NIR source placed behind an active-matrix organic light emitting diode (AMO-LED) display. The peak wavelength may be in the range of 740 nm-1000 nm, or may within the rage of 760-1000 nm, 780-1000 nm, 800-900 nm, 800-1000 nm, or the like. The OLED lamp may be disposed either behind or in front of the display. In another example, FIG. 6 shows a near infrared (NIR) light source disposed in front of the AMOLED, and a circular polarizer disposed between the AMOLED and the NIR light source. The peak wavelength may be in the range of 740 nm-1000 nm, or may within the rage of 760-1000 nm, 780-1000 nm, 800-900 nm, 800-1000 nm, or the like. In some embodiments, the NIR light source may be integrated into the display bezel. This arrangement may increase the bezel size.

Embodiments of the disclosed subject matter may include a quad pixel architecture. For example, red (R), green (G), blue (B), and near infra-red (NIR) sub-pixels may be used as the four sub-pixels in a quad pixel architecture. In some embodiments, a blue (B), green (G), green (G), and red (R) sub-pixels may be used as the four sub-pixels in a quad pixel architecture (i.e., BGGR), or blue (B) green (G), red (R) and red (R) pixels may be used as the four sub-pixels in a quad pixel architecture (i.e., BGRR). In some embodiments, the luminance and/or energy output of the NIR sub-pixels may all be similar or about the same, so that a driving circuit (e.g., a thin film transistor (TFT drive circuit) may not be needed for the NIR sub-pixels. That is, luminance of the quad pixel architecture may be adjusted by a global common voltage line, as opposed to a display sub-pixel whose luminance may be set by a data driver through a pixel driving circuit, every time a scan line is energized. That is, the NIR light may energize cells in the user, as opposed to providing visual information to the human eye.

In a conventional display with three primary colors, red (R), green (G), and blue (B), all three sub-pixels are usually configured in a stripe, each with its own data driver and a common scan or select line. With four sub-pixels, it is common to arrange them in a square or quad arrangement, and addressed by two (2) data drivers and two (2) scan or select lines.

RGB and NIR quad pixel arrangements may use four depositions. The NIR sub-pixel may not need its own backplane sub-pixel circuit, and may use a voltage source to control its energy output. That is, a backplane TFT density need not be increased.

In some embodiments, two green or two red sub-pixels quad architecture may be used, such as BGGR or BGRR, and one of the sub-pixels may be down-converted to NIR using a patterned quantum dot, NIR organic dye, and/or other suitable down-conversion medium.

A cavity may be used for a NIR pixel to improve efficiency. Blue (B'), and/or green (G'), and/or R' electron block layer (EBL) patterned layers may be extended over the NIR sub-pixel to render a desired NIR optical cavity length (between an anode of a device and emitting layer (EML)) without having to use additional fine metal mask steps (other than the NIR EML) in the NIR sub-pixel and without using down-conversion. Some embodiments may use no cavity for NIR pixels, so that there is no angular dependence to color shift with respect to a viewing angle. The B', G', and/or R' (EBL) patterned layers or some combination of one or more may extend over the NIR sub-pixel to render a desired optical cavity length. Some embodiments may use a low fill factor NIR pixel as NIR emitters, as they are very stable and the pixel may be typically used 30-60 minutes a day.

Embodiments of the disclosed subject matter may include a two, three, or four stack OLED. One stack may be a NIR emitting layer, and may be separately addressable. In this arrangement of having the NIR emitting layer as the top stack, the NIR may not need backplane control. Rather, the NIR emitting layer may be driven by a voltage source. That is, the arrangement may include a three terminal structure, with white light emitters from one series of EMLs disposed between two external electrodes, and NIR light being emitted from a NIR emitter disposed between another two external electrodes. In this arrangement, the cathode for the (visible) white-emitting stack may be transparent or semi-transparent. For example, a transparent or semi-transparent cathode may be at least 20% transmissive and preferably at least 40% transmissive across the visible spectrum. Preferably, an insulator may be placed above the white emitting stack cathode before the (NIR) anode, and the remainder of the NIR stack is placed on top. The white stack EMLs may be configured so as to maximize outcoupling and minimize angular dependence to color shift with respect to a viewing angle, as the NIR cathode may be the more dominant cavity node (along with the white stack anode cavity node).

FIG. 3 shows a device stack surface including an emissive layer and a near-infrared (NIR) emissive layer disposed between a first electrode and a second electrode according to an embodiment of the disclosed subject matter. As shown in FIG. 3, a device may include a first electrode, a second electrode, and at least one emissive layer and a near-infrared (NIR) emissive layer disposed in a stack arrangement between the first electrode and the second electrode. The emissive layer of the device may be a red (R) emissive layer, a green (G) emissive layer, a blue (B) emissive layer, a yellow emissive layer (Y), and/or a white emissive layer (W). At least one emissive layer may be at least semi-transparent.

The NIR light output by the NIR emissive layer may have a peak wavelength of 740 nm-1000 nm, 760-1000 nm, 780-1000 nm, 800-900 nm, 800-1000 nm, or the like. More than 50% of energy output of the NIR emissive layer may have a wavelength greater than 750 nm. The device may include at least one additional electrode disposed between the first electrode and the second electrode, where the NIR emissive layer is separately controllable from the at least one emissive layer. The NIR light output by the NIR emissive layer of the device may be a continuous wave having a predetermined optical power, or may be pulsed NIR light that may have a pulse frequency that is different from a frame rate or a clock frequency of the display device or the display surface. The maximum power density of the display device or the display surface for the NIR emissive layer may be 200 mW/cm$^2$. The optical power output of the NIR emissive layer per unit area of the display device or the display surface may be 2-200 mW/cm$^2$.

The NIR light may be output by the NIR emissive layer when the device is connected to an electrical power source other than a battery, where the electrical power source is connected to NIR pixels of the NIR emissive layer. A voltage of the electrical power source may determine an output energy of the NIR emissive layer. The NIR emissive layer may output the NIR light at a predetermined period of a day.

As shown in FIG. 3, the device may include at least one charge generation layer disposed between the emissive layer and the NIR emissive layer, or disposed between each of the emissive layers when the at least one emissive layer includes two or more emissive layers. An insulator may be disposed between the NIR layer of the stack arrangement and the at least one emissive layer. In some embodiments, the device may include a third electrode and a fourth electrode, where the third electrode and the fourth electrode are disposed between the first electrode and the second electrode.

Figure 4:
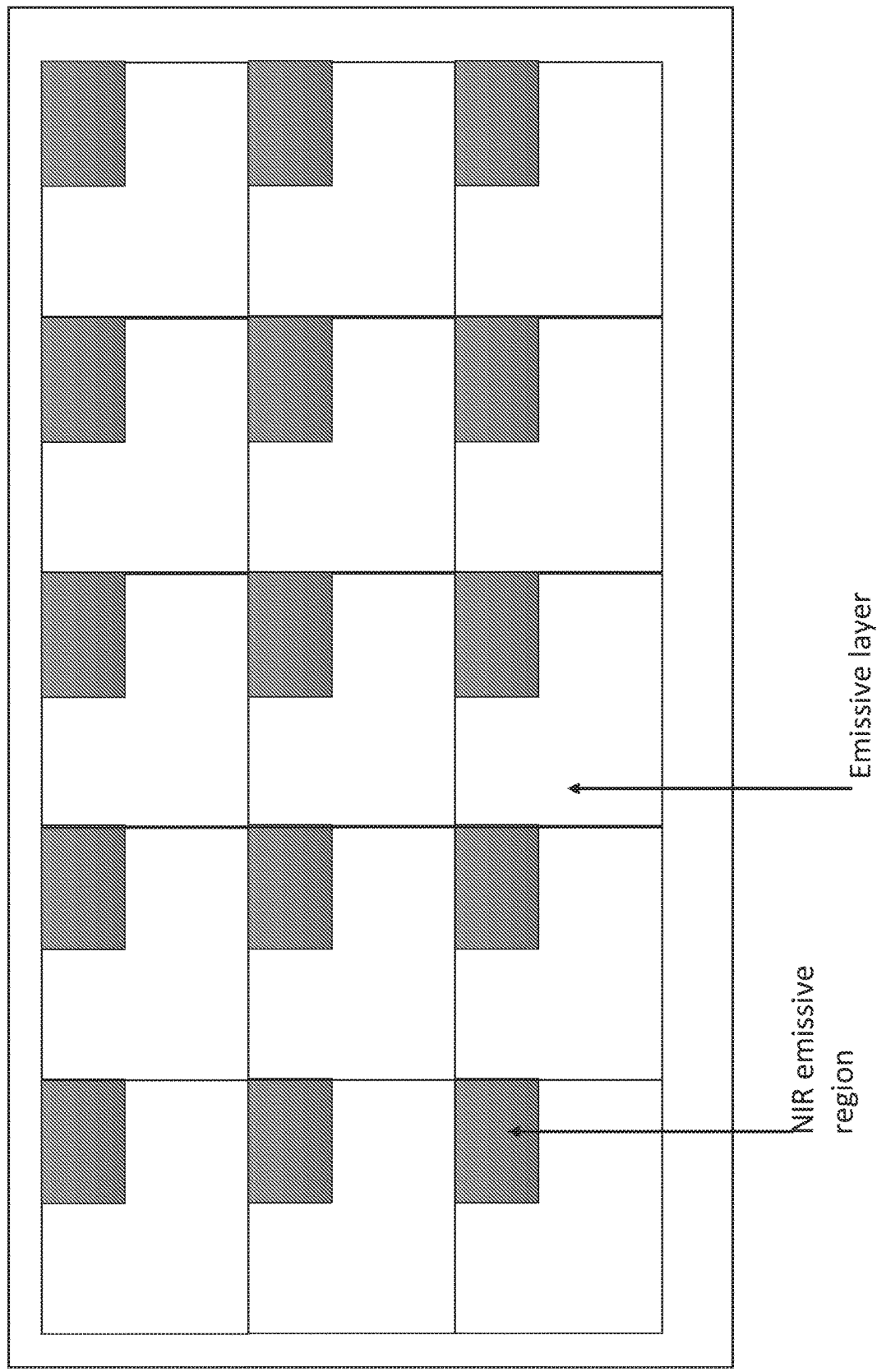
FIG. 4 shows a display where a portion of an emissive layer includes a NIR emissive region according to an embodiment of the disclosed subject matter.

FIG. 4 shows a display where a portion of an emissive layer includes a NIR emissive region according to an embodiment of the disclosed subject matter. As shown in FIG. 4, a device may include a display device or display surface having at least one emissive layer, where at least a portion of the at least one emissive layer includes a NIR emissive region. The emissive layer may be disposed between a pair of electrodes, such as shown in FIG. 3. The emissive layer may include a plurality of subpixels that may be red sub-pixels, green sub-pixels, blue sub-pixels, yellow sub-pixels, and/or white sub-pixels.

The NIR light output by the NIR emissive region may have a peak wavelength of 740-1000 nm, 760-1000 nm, 780-1000 nm, 800-900 nm, 800-1000 nm, or the like. More than 50% of energy output of the NIR emissive region of the device may have a wavelength greater than 750 nm. The NIR light output by the NIR emissive region may be a continuous wave having a predetermined optical power, or may be pulsed NIR light that has a pulse frequency that is different from a frame rate or a clock frequency of the display device or the display surface. The maximum power density of the display device or the display surface for the NIR emissive region may be 200 mW/cm$^2$. The optical power output of the NIR emissive region per unit area of the display device or the display surface may be 2-200 mW/cm$^2$.

The NIR light may be output by the NIR emissive region when the device is connected to an electrical power source other than a battery. That is, the photobiomodulation provided by the device may be operative when the device is connected to an external power source. The electrical power source may be connected to NIR pixels of the NIR emissive region, and a voltage of the electrical power source may determine an output energy of the NIR emissive region. The NW emissive region of the device may output the NIR light at a predetermined period of a day.

In some embodiments, a NIR light source may be placed behind the AMOLED active-matrix organic light emitting diode. In this arrangement, the AMOLED may be transparent or semi-transparent. This arrangement is preferred, as the NIR light source does not impact or degrade display image quality. In some embodiments, the NIR light source may be disposed in front of or on top of the AMOLED. This arrangement may reduce display brightness.

The NIR light source may use outcoupling enhancement. A transparent AMOLED may use transparent OLEDs. Alternatively, top emission OLEDs may be used, with transparent regions disposed between emissive regions. Transparent AMOLED may use switchable mirror anodes, as disclosed, for example, in U.S. patent application Ser. No. 16/197,406, filed Nov. 21, 2018 and incorporated by reference herein in its entirety. For normal operation with no IR light output, OLED anodes may be mirror-like and reflective, so as to provide top emission microcavity OLED output. If the display is off, and the NIR light source has output, the OLED anodes may be made transparent to increase display transparency.

The NIR light source may provide NIR light through the transparent OLED display. The fill-factor of red and green sub-pixels (e.g., from values used in a conventional non-transparent AMOLED display) may be reduced to improve display transparency (e.g., for transparent regions between emissive regions). In some embodiments, the NIR light source may be patterned to better couple to open spaces in transparent display, so photons are not wasted from areas of the light source that are covered by non-transparent regions of the display.

Display transparency may be achieved either through transparent sub-pixels, and/or transparent regions between sub-pixels (which may be bottom or top emission). Displays including NIR may include additional elements to mitigate any additional heat load imparted to the display due to the addition of the NIR lamp elements. Red sub-pixels may use a transparent anode. Green sub-pixels and blue sub-pixels may include a microcavity, by having a reflective anode, to provide increased saturated color. As the pixels may have a reflective anode, this may increase display transparency.

FIG. 5 shows a display device having a transparent active-matrix organic light emitting diode (AMOLED), and a near infrared (NIR) light source disposed behind the AMOLED according to an embodiment of the disclosed subject matter. As shown in FIG. 5, a device may include a display device or display surface having an active-matrix organic light emitting diode (AMOLED), and a near infrared (NIR) light source disposed behind or in front of or on top of the AMOLED. The NIR light source may have an area greater than 25% of an active area of the display device or display surface, and may have 75% of the active area of the display device. In some embodiments, as shown in FIG. 6, a circular polarizer may be disposed between the display device or display surface having the AMOLED and the NIR light source, where the NIR light source is disposed in front of the display device or display surface having the AMOLED.

In the embodiments shown in FIGS. 5-6, the NIR light source may be transparent to visible light (e.g., light having a wavelength of 400 nm-700 nm, or the like) when the AMOLED is disposed behind the NIR light source. The AMOLED may be transparent to NIR emission when the NIR light source is disposed behind the AMOLED. The transparent AMOLED may include transparent organic light emitting devices (OLEDs), and/or top emission OLEDs with transparent regions disposed between emissive regions.

The transparent AMOLED may include switchable mirror anodes. When there is no NIR light output from the NIR light source, OLED anodes may be reflective to providing top emission microcavity OLED output. When the display device is off, and the NIR light source has output, the OLED anodes may be configured to be transparent. The display device may be configured to be transparent by using transparent sub-pixels, and/or transparent regions between the sub-pixels. The red sub-pixels of the display device may include a transparent anode, and green and blue sub-pixels of the display device include a microcavity.

The NIR light source may be patterned within each pixel of the display device or the display surface. The NIR light source may include an outcoupling device that may be disposed between the NIR light source and the display device. The device may include a heat dissipation device configured to dissipate heat from the NIR light source.

The NIR light source may output continuous wave or pulsed NIR light that has a pulse frequency that is different from a frame rate or a clock frequency of the display device or the display surface. The NIR light source may be segmented into regions, and each region may be illuminated in sequence. The NIR light source may output NIR light when the device is connected to electrical power source other than a battery. The electrical power source may be connected to NIR pixels of the NIR light source, and a voltage of the electrical power source may determine an output energy of the NIR light source. The NIR light source may output NIR light at a predetermined period of a day. The NIR light source may be an OLED (organic light emitting device) light source, a Quantum Dot light source, and/or a micro-LED (light emitting device) source. NIR light output by the NIR light source may have a peak wavelength of 740 nm-900 nm. More than 50% of energy output of the NIR source may have a wavelength greater than 750 nm.

In embodiments of the disclosed subject matter shown in FIGS. 3-6, the NIR or IR photobiomodulation light may be pulsed (e.g., pulsed 10 Hz to 100 Hz, or any other suitable frequency), or may be continuous wave (CW). NIR light sources may be segmented into regions, with each region illuminated in sequence. For example, if a NIR light source is segmented into four regions, each region may have a 25% duty cycle. This arrangement may reduce peak power requested from any power supply.

As the photobiomodulation light sources (e.g., NIR light source) may consume power, some embodiments of the NIR light source may be activated when the device is connected to electrical power (i.e., to save battery power), and otherwise refrain from activating the NIR when the device is operating based on battery power. In some embodiments, the NIR may be activate later in day, because red or NIR light may increase melatonin production, and 30-60 minutes exposure a day may be all that is needed. In some embodiments, blue lights may be added to an OLED light source of a device to counteract seasonal affective disorder (SAD).

In some embodiments, the display may be a LCD (liquid crystal display) or microLED display (micro light emitting diode display) with a NW light source disposed in the backlight of the LCD. In some embodiments, a NIR light source may be included with an emissive EL quantum dot display.

In some embodiments, an IR or NIR light source may be integrated with a white board or other large area device near which people sit or stand.

In the embodiments disclosed throughout, the photobiomodulation illumination source may be from an OLED, or Quantum Dot or micro-LED (micro-light emitting diode) source. If the photobiomodulation illumination device uses a NIR light source transmitting through a transparent display, the NIR light source be an OLED, quantum dot, or LED.

In some embodiments, the photobiomodulation illumination source may be integrated into eye glasses. The glasses may be made substantially transparent (or even corrective), and the NIR OLED light source (e.g., emitting at a peak wavelength of 800-850 nm, or the like) may be coated over each lens using a transparent OLED architecture. A thin film battery and control circuitry may be incorporated into the frame of the glasses to allow the user to perform normal functions and see through the lenses of the glasses while they emit NIR to the wearer. In this arrangement, the OLED may be a light source, rather than a display rendering visual information.

In some embodiments, a photobiomodulation (PBM) light source may be with an addressable active-matrix display, whereby the PBM source may have an area greater than 50% of the display active area. In some embodiments, a photobiomodulation (PBM) light source may be integrated with an addressable active-matrix display, whereby the PBM source emits in the infra-red. Some embodiments may include a substantially transparent wearable photobiomodulation (PBM) light source.

It is understood that the various embodiments described herein are by way of example only, and are not intended to limit the scope of the invention. For example, many of the materials and structures described herein may be substituted with other materials and structures without deviating from the spirit of the invention. The present invention as claimed may therefore include variations from the particular examples and preferred embodiments described herein, as will be apparent to one of skill in the art. It is understood that various theories as to why the invention works are not intended to be limiting.

We claim:

1. A device comprising:
    an emissive organic light emitting diode (OLED) device, comprising:
        a first electrode;
        a second electrode;
        a display device or display surface including at least one emissive layer and a near-infrared (NIR) emissive layer disposed in a stack arrangement between the first electrode and the second electrode, wherein the NIR emissive layer includes a plurality of segments for emitting a NIR light; and
        control circuitry configured to control a duty cycle of the display device or the display surface to pulse the NIR light output by the plurality of segments of the NIR emissive layer, wherein at least one of the plurality of segments emits the NIR light during the duty cycle and the NIR light is emitted in sequence from different segments at different times,
        wherein the NIR light is emitted from the NIR emissive layer through the at least one emissive layer, or visible light is emitted from the at least one emissive layer through the NIR emissive layer,
        wherein the NIR light output by the NIR emissive layer has a peak wavelength of 740 nm-1000 nm, and
        wherein an average power density of the display device or the display surface for the NIR emissive layer is between 50-200 mW/cm$^2$.

2. The device of claim 1, wherein more than 50% of energy output of the NIR emissive layer has a wavelength greater than 750 nm.

3. The device of claim 1, further comprising at least one charge generation layer disposed between the at least one emissive layer and the NIR emissive layer, or disposed between each of the emissive layers when the at least one emissive layer includes two or more emissive layers.

4. The device of claim 1, further comprising:
at least one additional electrode disposed between the first electrode and the second electrode,
wherein the NIR emissive layer is separately controllable from the at least one emissive layer.

5. The device of claim 1, further comprising:
a third electrode; and
a fourth electrode,
wherein the third electrode and the fourth electrode are disposed between the first electrode and the second electrode, and
wherein an insulator is disposed between the NIR layer of the stack arrangement and the at least one emissive layer.

6. The device of claim 1, wherein the at least one emissive layer is an organic emissive layer, and the near-infrared (NIR) emissive layer is an organic emissive layer.

* * * * *